(12) United States Patent
Duncan

(10) Patent No.: US 8,394,020 B2
(45) Date of Patent: Mar. 12, 2013

(54) SKIN LAXITY MEASUREMENT SYSTEM

(75) Inventor: Diane I. Duncan, Fort Collins, CO (US)

(73) Assignee: American Network of Lipolysis, LLC, Fort Collins, CO (US)

( * ) Notice: Subject to any disclaimer, the term of this patent is extended or adjusted under 35 U.S.C. 154(b) by 399 days.

(21) Appl. No.: 12/800,080

(22) Filed: May 7, 2010

(65) Prior Publication Data

US 2010/0286493 A1 Nov. 11, 2010

Related U.S. Application Data

(60) Provisional application No. 61/215,742, filed on May 8, 2009.

(51) Int. Cl.
*A61B 5/00* (2006.01)

(52) U.S. Cl. ........................................ 600/306; 600/300

(58) Field of Classification Search ............ 33/783–784, 33/27.03, 501.06, 501.6, 511, 512, 810–812, 33/818–820, 823–824, 828; 600/306
See application file for complete search history.

(56) References Cited

U.S. PATENT DOCUMENTS

| | | | | |
|---|---|---|---|---|
| 735,935 A | * | 8/1903 | Billnigs | 33/472 |
| 888,070 A | * | 5/1908 | Dissell | 33/464 |
| 3,008,239 A | | 11/1961 | Lange | |
| 4,233,743 A | * | 11/1980 | Flick | 33/512 |
| 2005/0235517 A1 | * | 10/2005 | John et al. | 33/784 |

* cited by examiner

*Primary Examiner* — Michael Kahelin
*Assistant Examiner* — Mitchell Alter
(74) *Attorney, Agent, or Firm* — Craig R. Miles; CR Miles PC

(57) ABSTRACT

A skin laxity measurement system which provides a skin laxity measurement tool and methods of measuring skin laxity.

12 Claims, 4 Drawing Sheets

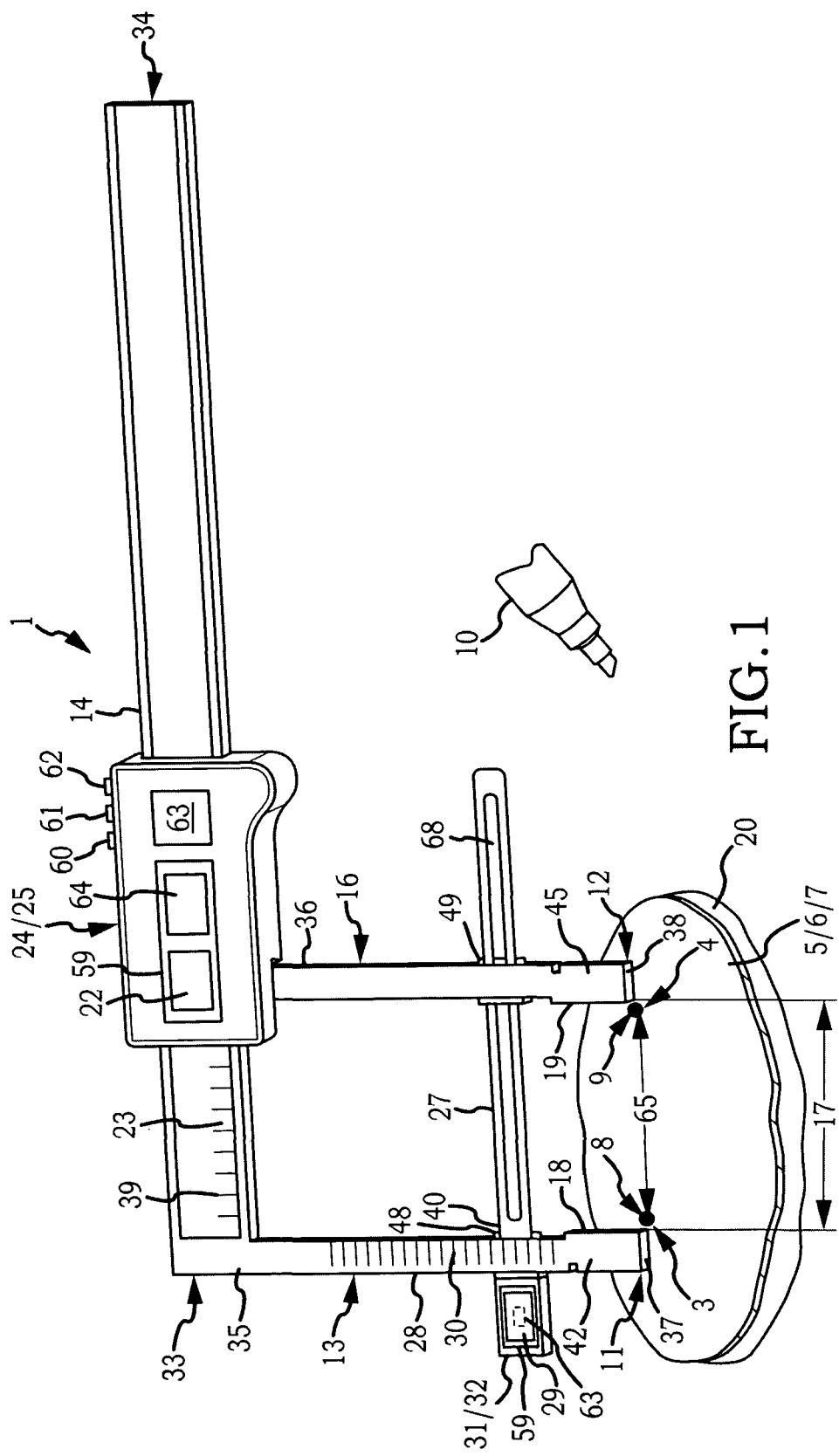

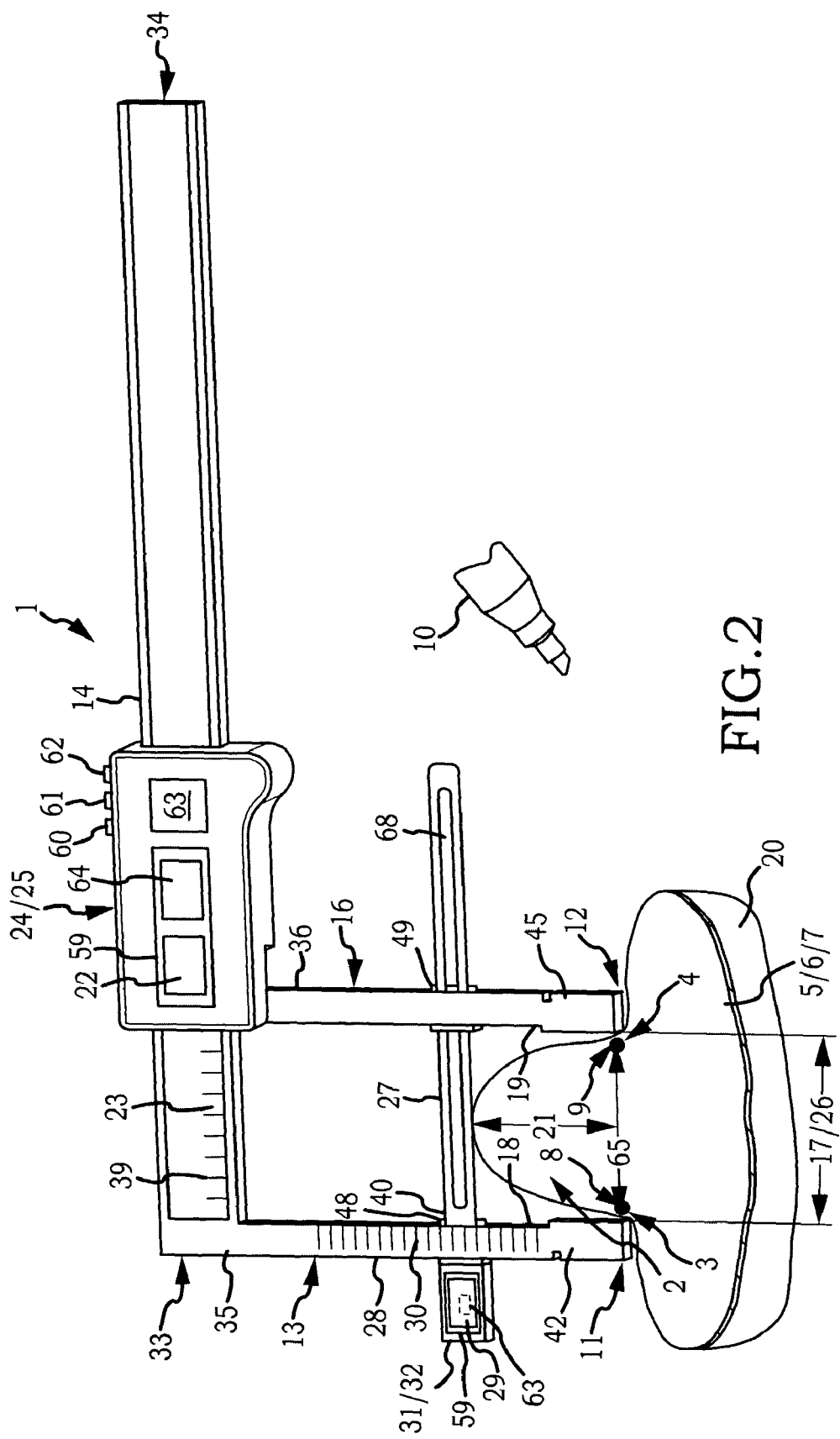

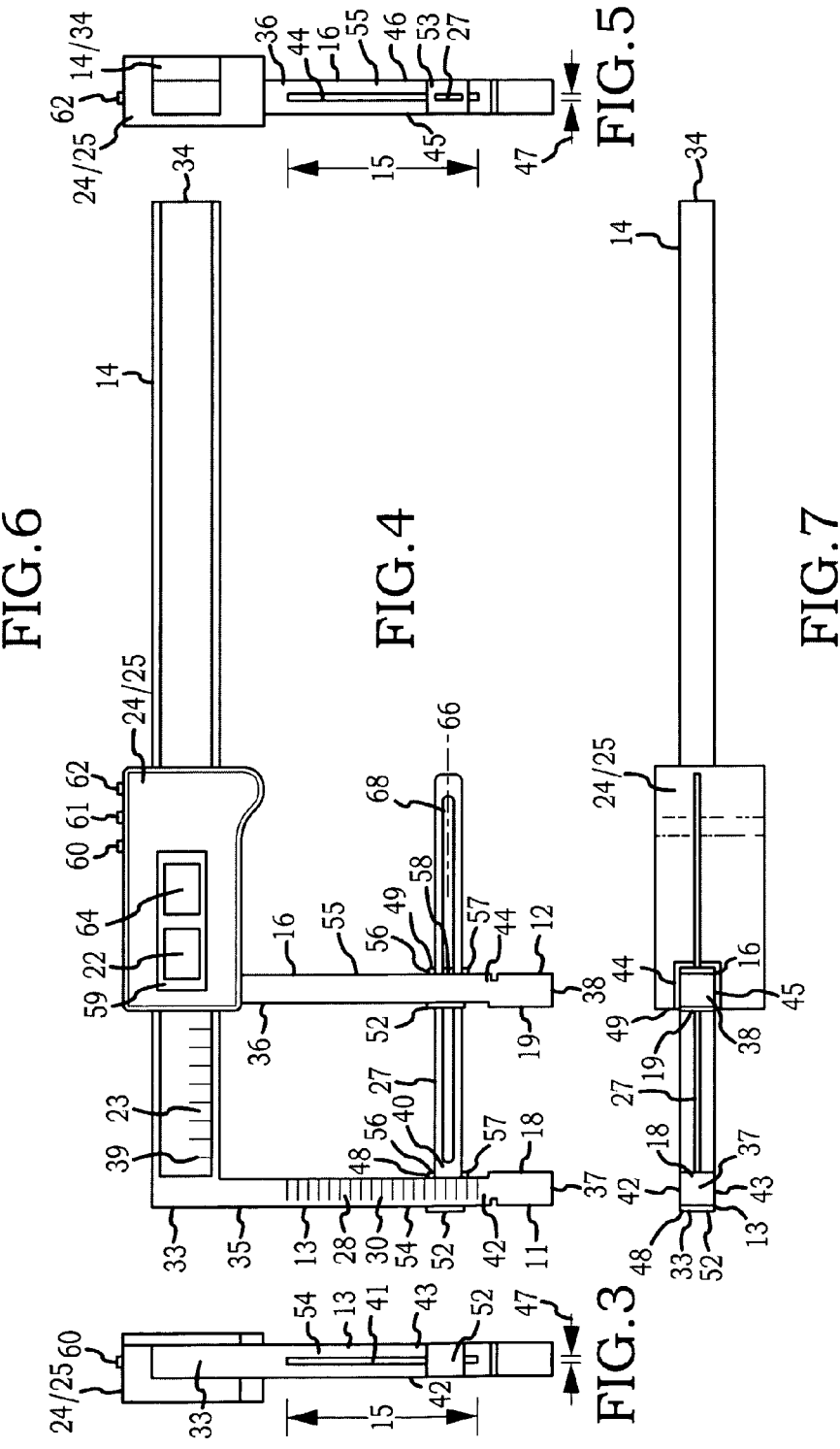

SKIN LAXITY MEASUREMENT SYSTEM

This United States Non-Provisional patent application claims the benefit of U.S. Provisional Patent Application No. 61/215,742, filed May 8, 2009, hereby incorporated by reference in the entirety herein.

I. BACKGROUND

A skin laxity measurement system which provides a skin laxity measurement tool and methods of measuring skin laxity.

Conventionally, skin fold measurements are taken by drawing together a portion of the skin and the flexible subtissue below the skin at certain selected positions on the body and the limbs. For example, these measurements can be taken at the back of the arm (tricep) and at the hip (iliac crest). For men, additional measurements may be taken at the front of the arm (bicep) and at the upper back (subscapular). The sum of these measurements can then compared with a chart to determine the relative amount of fat.

A substantial problem with conventional skin fold measurement can be that because of the resiliency of the skin and the subsurface layer of fat, the measurements obtained will necessarily be a function of the pressure applied by the caliper. To overcome this problem a standard pressure for taking skin-fold measurements is often utilized and constant pressure calipers are available.

However, there are problems with constant pressure calipers designed to measure skin folds. First, constant pressure calipers such as those described in U.S. Pat. No. 3,008,239 to Lange utilize a spring to apply pressure between the jaws and the pressure generated can vary proportionately with the distance to which it is extended. Second, to overcome this problem, constant pressure calipers can be relatively complex. For example, Lange employs a gear and lever system to obtain constant pressure over the range of distances through which the jaws may be extended. Third, due to the aforementioned complexity, constant pressure calipers can be prohibitively expensive. Fourth, constant pressure calipers urge the skin and subsurface layer of fat together to allow assessment of the relative amount of fat but do not assess the amount of laxity in the folded skin. So while there may be a decrease in the fat underlying the skin there may still be noticeable loose skin and this degree of laxity may not be measurable with conventional constant pressure calipers.

Accordingly, the instant a skin laxity measurement system and skin laxity measurement tool and methods of measuring skin laxity provides a solution to the problems associated with conventional calipers for skin fold measurement.

II. SUMMARY OF THE INVENTION

Accordingly, a broad object of the invention can be to provide a skin laxity measurement tool which allows assessment of a skin fold (also referred to as "a tissue fold") with respect to both tissue fold width (or tissue fold thickness) when urged together under pressure and with respect to the resulting tissue fold height which allows assessment of skin laxity (or skin looseness).

Another broad object of the invention can be to provide a method of comparative measurement of tissue fold width and tissue fold height which can be utilized to assess the amount of fat underlying the skin and skin laxity.

Naturally, further objects of the invention are disclosed throughout other areas of the specification, drawings, photographs, and claims.

III. A BRIEF DESCRIPTION OF THE DRAWINGS

FIG. 1 shows a method of using a particular embodiment of a skin laxity measurement tool.

FIG. 2 shows a method of using a particular embodiment of a skin laxity measurement tool to determine tissue fold width and tissue fold height.

FIG. 3 shows first end view of a particular embodiment of a skin laxity measurement tool.

FIG. 4 shows a side view of a particular embodiment of a skin laxity measurement tool.

FIG. 5 shows a second end view of a particular embodiment of a skin laxity measurement tool.

FIG. 6 shows a top view of a particular embodiment of a skin laxity measurement tool.

FIG. 7 shows a bottom view of a particular embodiment of a skin laxity measurement tool.

IV. DETAILED DESCRIPTION OF THE PREFERRED EMBODIMENTS

Figure 8:
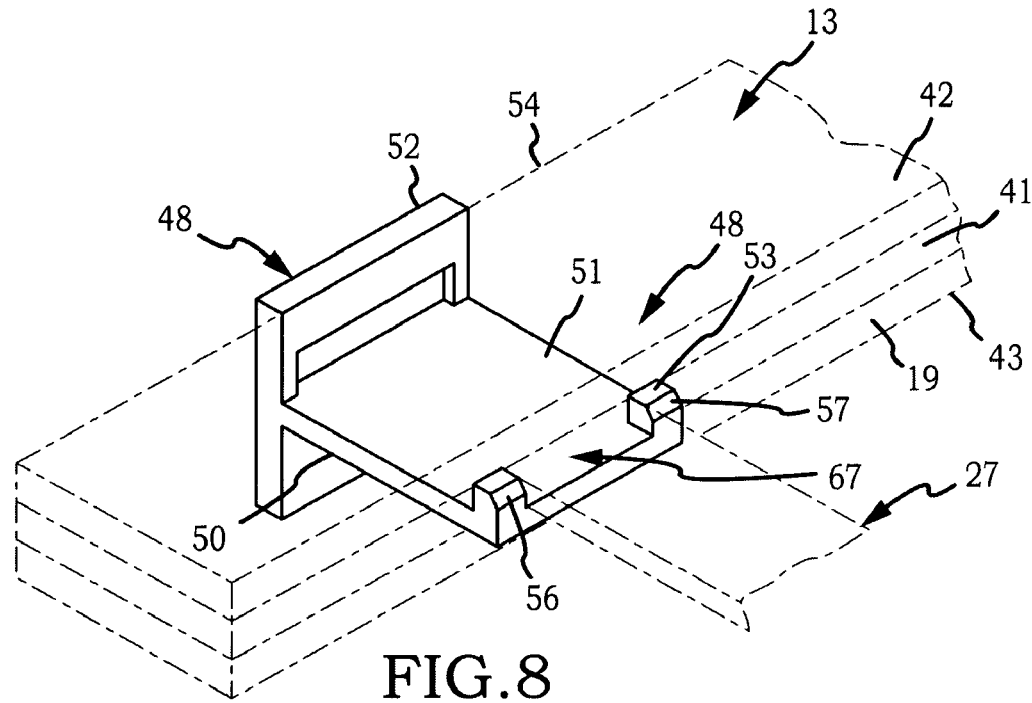
FIG. 8 shows an enlarged view of a particular embodiment of a cross member guide.
Figure 9:
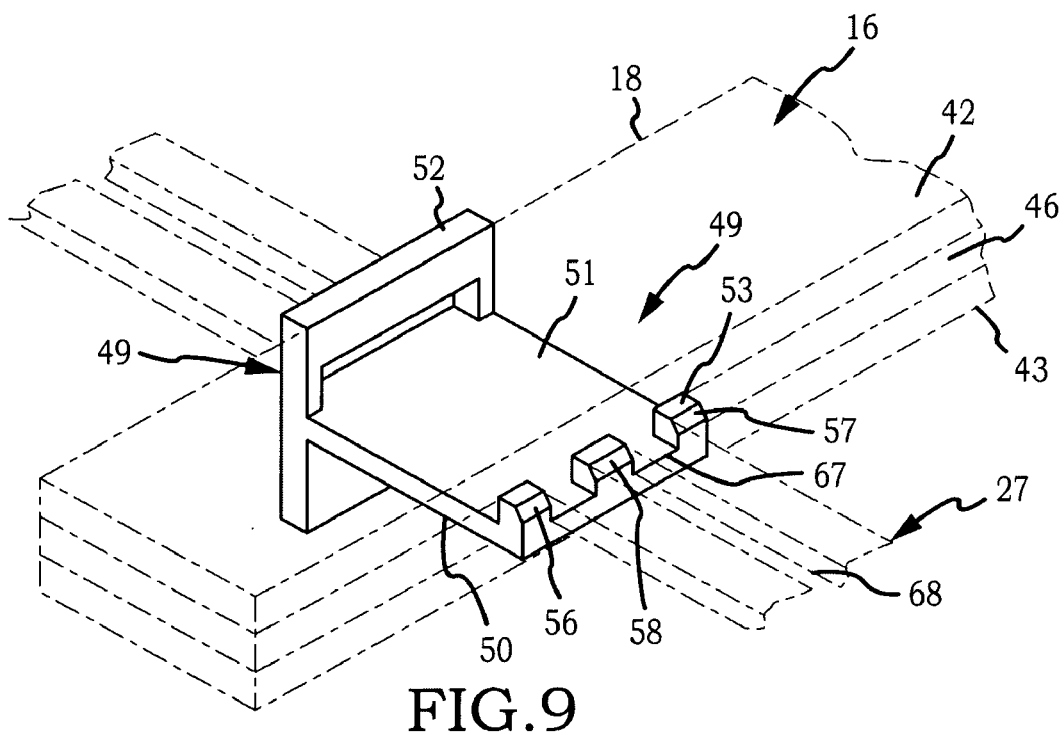
FIG. 9 shows an enlarged view of a particular embodiment of a cross member guide.

A skin laxity measurement system which provides a skin laxity measurement tool and methods of measuring skin laxity.

First, referring primarily to FIGS. 1 and 2, which show a particular method of using an embodiment of a skin laxity measurement tool (1) to make a skin laxity measurement. The term "skin laxity measurement" for the purposes of this invention means a measurement of a tissue fold (2) using the skin laxity measurement tool (1) as described herein. The tissue fold (2) can generated by opposed forcible urging at a first skin location (3) and a second skin location (4) on the external surface (5) of the skin (6) of an animal (7). A first skin location (3) and a second skin location (4) a distance apart on the external surface (5) of the skin (6) of an animal (7) which can be identified with a corresponding first mark (8) and a second mark (9) for subsequent skin laxity measurement between the first skin location (3) and the second skin location (4). The term "animal (7)" for the purposes of this invention generally includes all animals which have a skin (6) structure that can be measured as below described and without limitation to the forgoing includes humans, dogs, cats, rats, mice, horses, cows, sheep, or the like (the hair or fur being removed as necessary to take the skin laxity measurement). The term "skin (6)" for the purposes of this invention generally includes the soft outer covering of an animal and the flexible sub-tissue below the outer covering. The first skin location (3) and the second skin location (4) can each have a location anywhere on the external surface (5) of the skin (6) which affords an area of skin (6) measurable with a constructional form of the skin laxity measurement tool (1); and without limitation of the forgoing, typically the distance (65) between the first skin location (3) and the second skin location (4) will be in the range of about one half inch and about six inches.

A first mark (8) can be applied to the first skin location (3) and a second mark (9) can be applied to the second skin location (4) to provide consistency as to placement of the skin laxity measurement tool (1) for or between repeated skin laxity measurements. The first mark (8) and the second mark (9) can be made by any marking means (10) capable of producing a perceivable first mark (8) or second mark (9) at each of the first skin location (3) and the second skin location (4). Without limitation to the forgoing, the marker (10) can include a pen, grease pencil, felt tip marker, stylus, dropper, imprinter, or the like, which by operation results in a visually perceivable (whether directly or indirectly by use of visualization means such as black light) first mark (8) or second mark (9) at the corresponding first skin location (3) and second skin location (4) on the external surface (5) of the skin (6)(or in certain instances by tattoo proximate the external surface of the skin). The first skin location (3) and the second location (4) can be remarked between skin laxity measurements or the first mark (8) and the second mark (9) can be sufficiently resistant to removal to allow a plurality of skin laxity measurements to be taken using the skin laxity measurement tool (1) over a duration of time without refreshing the marks (8)(9). The period of time over which a plurality of skin laxity measurements can be taken is not fixed and can be from several minutes to several years depending upon the skin laxity measurement application.

Again primarily referring to FIGS. 1 and 2, the skin laxity measurement tool (1) can be positioned to contact a first arm terminal (11) on the external surface (5) of the skin (6) of the animal (7) at the first skin location (3) and to contact a second arm terminal (12) on the external surface (5) of the skin (6) at the second skin location (4). Contact of the first arm terminal (11) on the external surface (5) of the skin (6) at the first skin location (3) and contact of the second arm terminal (12) on the external surface (5) of the skin (6) at the second skin location (4) can each result in sufficient fixed engagement of the first arm terminal (11) with the external surface (5) of the skin (6) at the first skin location (3) and sufficient fixed engagement of the second arm terminal (12) with the external surface (5) of the skin (6) at the second skin location (4) for operation of the skin laxity measurement tool (1).

Again referring primarily to FIGS. 1 and 2, the first arm terminal (11) can be responsive to movement of a first arm (13) slidely coupled to a first linear measurement guide (14) and the second arm terminal 12 can be responsive to movement of a second arm (16) slidely coupled to the first linear measurement guide (14). Certain embodiments of the skin laxity measurement tool (1) can have either the first arm (13) or the second arm (16) coupled in fixed relation to the first linear measurement guide (14). As to the particular embodiment of skin laxity measurement tool (1) shown in FIGS. 1 and 2, the first arm (13) is coupled in fixed relation to the first linear measurement guide (14) while the second arm (16) moves along the first linear measurement guide (14), or otherwise travels in relation to the first arm (13) to increase or decrease a distance (17) between opposed inner surfaces (18) (19) of the first arm (13) and the second arm (16).

Now referring primarily to FIG. 2, the tissue fold (2) can be generated between the inner surfaces (18)(19) of the first arm (13) and the second arm (16) of the skin laxity measurement tool (1) by maintaining contact of the first arm terminal (11) at the first location (3) on the external surface (5) of the skin (6) and maintaining contact of the second arm terminal (12) at the second location (4) on the external surface (5) of the skin (6) during operation of the skin laxity measurement tool (1) to reduce the distance (17) between the opposed inner surfaces (18)(19) of the first arm (13) and the second arm (16).

The distance (17) between the opposed inner surfaces (18) (19) of the first arm (13) and the second arm (16) can be reduced by sufficient urging of the first arm (13) or the second arm (16) (depending upon the embodiment) to slide, move along, or otherwise travel in relation to a first linear measurement guide (14) in the direction which reduces the distance (17) between the opposed inner surfaces (18)(19) of the first arm (13) and the second arm (16). Reduction of the distance (17) between the opposed inner surfaces (18)(19) of the first arm (13) and the second arm (16) while maintaining contact of the first arm terminal (11) with the external surface (5) of the skin (6) at the first skin location (3) and maintaining contact of the second arm terminal (12) with the external surface (5) of the skin (6) at the second skin location (4) correspondingly reduces the distance (65) between the first skin location (3) and the second skin location (4) on the external surface (5) of the skin (6) to induce upward movement or folding of the skin (6) and the associated layers (20) between the opposed inner surfaces (18)(19) of the first arm (13) and the second arm (16) (the "tissue fold")(2). The configuration of the tissue fold (2) or the amount of upward movement of the skin (6) (the "tissue fold height"(21))(see specifically FIG. 2) between the opposed inner surfaces (18) (19) of the first arm (13) and the second arm (16) can be to a certain degree dependent on the amount of reduction of distance (17) between opposed inner surfaces (18)(19) of the first arm (13) and the second arm (16). Understandably, the distance (17) between opposed inner surfaces (18)(19) of the first arm (13) and second arm (16) can be established to generate a tissue fold (2) having a tissue fold width (26) and a tissue fold height (21) sufficient for the particular application.

Again primarily referring to FIGS. 1 and 2, as the distance (17) between opposed inner surfaces (18)(19) of the first arm (13) and the second arm (16) increases or decreases a corresponding distance value (22) can be obtained by reference to a first graduated scale (23) coupled to the first linear measurement guide (14) or by reference to a displayed distance value (22) of an analog distance calculator (24) or digital distance calculator (25). Upon generation of the tissue fold (2) between the opposed inner surfaces (18)(19) of the first arm (13) and the second arm (16) sufficient for the application, the distance value (22) corresponding to the tissue fold width (26) can be obtained by visual reference to the first graduated scale (23) coupled to the first linear measurement guide (14) or visual reference to distance value (22) provided by the analog distance calculator (24) or digital distance calculator (25). Alternately, the distance (17) between the opposed inner surfaces (18)(19) of the first arm (13) and the second arm (16) can be established at a pre-determined distance value (22) to generate a corresponding configuration of the tissue fold (2) or the distance (17) between the opposed inner surfaces (18) (19) can be established at a distance value (22) corresponding to a pre-determined tissue fold height (21).

Again referring to FIGS. 1 and 2, a cross member (27) can be slidely coupled in substantially perpendicular relation to the first arm (13) and the second arm (16)(or in substantially perpendicular relation to the opposed inner surfaces (18)(19) of the first arm (13) and the second arm (16)) to allow movement in relation to the first arm terminal (11) and the second arm terminal (12) and a second linear measurement guide (28). Upon generating the tissue fold (2) between the opposed inner surfaces (18)(19) of the first arm (13) and the second arm (16) (to the extent necessary based on the application as above described) the cross member (27) can be moved in relation to the second linear measurement guide (28) to contact the tissue fold (2) to establish a height in relation to the first arm terminal (11) (or both the first and second arm terminals (11)(12)) which corresponds to the tissue fold height (21). A height value (29) corresponding to the tissue fold height (21) can be obtained from the visual reference to a second linear graduated scale (30) or visual reference to a height value (29) provided by an analog height value calculator (31) or digital height value calculator (32). As an example, the height value (29) can be as little as about one millimeter to several centimeters with the cross member (27)

as to particular embodiments of invention being adjustable in relation to the first arm terminal (11) and the second arm terminal (12) essentially to the unfolded skin height. Alternately, the cross member (27) can be established at a predetermined height value (21) to generate the corresponding tissue fold width (26) between the opposed inner surfaces (18)(19) of the first arm (13) and the second arm (16).

Now primarily referring to FIGS. 3-7, a particular embodiment of the skin laxity measurement tool (1) is shown which provides a first linear measurement guide (14) having a length disposed between a first end (33) and a second end (34). The first arm (13) can be coupled proximate the first end (33) of the first linear measurement guide (14). In the particular embodiment of the skin laxity measurement tool (1) shown in FIGS. 3-7, the first arm (13) can be fixedly coupled by a first arm end (35) proximate the first end (33) of the a first linear measurement guide (14); however, the invention is not so limited and certain embodiments may provide a slidely coupled or incrementally adjustably coupled first arm (13) which can be positioned at a location between the first end (33) and the second end (34) of the a first linear measurement guide (14). The first arm (13) can have a length disposed between the first arm end (35) coupled to the first linear measurement guide (14), as above described, and a first arm terminal (11). The first arm terminal (11) while shown in FIGS. 3-7 as having terminal face (37) of substantially square configuration (FIGS. 1 and 2 showing a rectangular configuration); is not so limited, and the configuration of the terminal face (37) can be for example rectangular, semicircular, circular, the apex of a cone, or the like depending on the application.

Again referring primarily to FIGS. 3-7, a second arm (16) can be coupled by a second arm end (36) to the first linear measurement guide (14). In the particular embodiment shown by FIGS. 3-7, the second arm (16) can be slidely coupled to allow movement along the first linear measurement guide (14). The second arm (16) can have a length disposed between the second arm end (36) slidely coupled to the first linear measurement guide (14), as above described, and a second arm terminal (12). The second arm terminal (12) while shown in FIGS. 3-7 as having a terminal face (38) of substantially square configuration (shown in FIGS. 1 and 2 as rectangular); is not so limited, and the configuration of the terminal face (38) can be for example rectangular, semicircular, circular, the apex of a cone, or the like depending on the application.

The first arm (13) and the second arm (16) can each provide an inner face (18)(19) disposed in opposed relation a distance (17) apart adjustable (or in movable relation) by sliding engagement of either the first arm (13) or the second arm (16), or both depending upon the embodiment of the skin laxity measurement tool (1), in relation to the first linear measurement guide (14). Typically, as above described, the first arm (13) can have a fixed location and the second arm (16) slidely engages the first linear measurement guide (14) to adjust the distance (17) between the inner faces (18)(19) disposed in opposed relation. A first graduated scale (23) can be coupled to the first linear measurement guide (14) between the first end (33) and the second end (34). The first graduated scale (23) can as to certain embodiments can have visually perceivable measurement indicia (39) (or a plurality of measurement indicia) located to set out units such as millimeters, centimeters, inches or fractions of an inch or otherwise alignable with the position of the first arm (13) or the second arm (16) to allow determination of a distance value (22) corresponding to the distance (17) between the inner faces (18)(19) disposed in opposed relation. As to other embodiments, the first graduated scale (23) can provide other measurement indicia (39) capable of translation into the distance value (17) by an analog distance calculator (24) or a digital distance calculator (25) each having mechanical components or electrical components which translate measurement indicia such as teeth per unit distance or revolutions of a circular member or otherwise into a viewable or displayed distance value (22). A particular embodiment of the skin laxity measurement tool (1) can be produced by modification of a Carrera Precision Titanium Series Professional Digital LCD 24 Inch Caliper, Model CP 5924 and by addition of further elements as described herein depending on the application.

Again referring primarily to FIGS. 3-7, embodiments of the skin laxity measurement tool (1) can further include a cross member (27) slidely coupled to a second linear measurement guide (28) of either the first arm (13) or the second arm (16), or both of the first arm (13) and the second arm (16). As shown in FIGS. 3-7, a first cross member end (40) of the cross member (27) can be configured to slidely engage the second linear measurement guide (28) of the first arm (13) to allow positioning of the cross member (27) at a location between the first arm end (35) and the first arm terminal (11) or positioning of the cross member (27) a distance from the terminal face (37) of the first arm (13) and the terminal face (38) of the second arm (16). As to certain applications, the cross member (27) can have sufficient slidable engagement with the first arm (13) or the second arm (16), or both, to allow measurement of the tissue fold height (21) from essentially the unfold skin height to several centimeters depending upon the embodiment of the skin laxity measurement tool (1).

Now referring primarily to FIGS. 3, 4, 8 and 9, a particular embodiment of the cross member (27) can be slidely coupled to the first arm (13) and slidely coupled to the second arm (16) by provision of a first slot (41) between the opposed faces (42)(43) of the first arm (13) and a second slot (44) between the opposed faces (45)(46) of the second arm (16). The first slot (41) and the second slot (44) can commence proximate the corresponding first arm terminal (11) and second arm terminal (12) and terminate proximate the corresponding first arm end (35) and second arm end (36) (the "slot height" (15)). The slot height (15) can be adjusted based on the embodiment of the a skin laxity measurement tool (1) and may for example have a slot height (15) which corresponds with the length of second linear graduated scale (30). The first slot (41) and the second slot (44) can have sufficient slot width (47) to receive the cross member (27) in substantially perpendicular relation to the first arm (13) and the second arm (16). Typically, the first slot (41) and the second slot (44) will have the same or similar dimensional form; however, the invention is not so limited, and the first slot (41) and the second slot (44) can have substantially different dimensional forms depending on the application. The first cross member end (40) can be configured to slidely mate with the configuration of the first slot (41) and a portion of the cross member can be configured to slidely mate with the configuration of the second slot (44) to allow the cross member (27) to travel in substantially perpendicular relation to the first arm (13) and the second arm (16). Embodiments of the a skin laxity measurement tool (1) can further include one or more cross member guides (48)(49) (see also FIGS. 8 and 9 which show enlarged renderings of the cross member guides (48)(49)) each having an external guide surface (50) which slidely mates with the corresponding first slot (41) and second slot (44). Each of the cross member guides (48)(49) can further include an internal guide surface (51) configured to mate with corresponding portions of the cross member (27) and dispose the cross member (27) in proper relation with the first arm (13) and the second arm (16) as each of the cross member guides (48)(49) move within the first slot (41) and the second slot (44). Each of the cross member guides (48)(49) can further include radial guide elements (52)(53) which extend radially outward from the external guide surface (50) to sufficiently slidely engage the outer surfaces (54)(55) and the opposed inner surfaces (18)(19) of the corresponding first arm (13) and second arm (16) to limit movement of the cross member (27) along the longitudinal axis (66) of the cross member (27). Each of the cross member guides (48)(49) can further include a cross member anti-pivot element (67) which engages the cross member (27) to prevent rotation of the cross member (27) proximate the slidable coupling with the first arm (13) and the second arm (16). The anti-pivot element (67) can as shown in FIG. 8 can take the form of a bifurcation of the a radial guide element (53) into a pair of flanges (56)(57) which engage opposite sides of the cross member (27) to fix the cross member (27) in substantially perpendicular relation with the first arm (13). Certain embodiments of the anti-pivot element (67) (see FIG. 9) can further include projection element (58) between the pair of flanges (56)(57) of the bifurcation of the radial guide element (53) which travels in a corresponding cross member slot (68). As to certain embodiments of the cross member guides (48)(49), the external guide surface (50), the internal guide surface (51), the radial guide elements (52)(53), and the pair of flanges (56)(57) and the projection element (58) can be made in one piece and as to certain embodiments the cross member (27) and certain parts of the cross member guides (48)(49) can be made as one piece. The particular example of the cross member (27) and the manner of slidely engaging the cross member (27) to the first arm (13) and the second arm (16) in corresponding slots (41)(44) is not intended to be limiting with respect to the numerous and varied configurations of the cross member (27) that can be utilized to slidely mate or engage the first arm (13) or the second arm (16), or both to perform the same function.

Now referring primarily to FIGS. 1 and 2, certain embodiments of the a skin laxity measurement tool (1) can further include an analog height calculator (31) or a digital height value calculator (32) in addition to or in replacement of the second graduated scale (30) which can translate movement of the cross member (27) in relation to the first arm (13) or the second arm (16) (or the first arm terminal (11) or the second arm terminal (12)) into a viewable height value (29). The digital height calculator (32) (and the digital distance calculator (25) above described can each provide a display panel (59), and certain embodiments can further provide one or more of a first switch (60) for toggling between measurements in inches and millimeters, a second switch (61) for turning the device on or off, and a third switch (62) for calibrating the digital distance calculator (25) or the digital height calculator (32) (switches shown only on the digital distance calculator (25)) when the opposed inner surfaces (18)(19) abut. Although the digital distance calculator (25) and the digital height calculator (32) shown are described by way of example with three switches performing specific functions, it should be understood that the digital measuring device can be embodied in other ways without departing from the scope of the present invention. As a non-limiting example, the second switch (61) for turning the digital distance calculator (25) or digital height calculator (32) on or off is not necessary for a solar powered digital distance or height calculators (25)(32). Additionally, the digital height calculator (32) and the digital distance calculator (25) can further include a tissue fold comparison element (63) which functions to provide viewable tissue fold values (64) related to the various relationships derivable between tissue fold width (26) and tissue fold height (21).

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a first skin location" refers to one or more of first skin location. As such, the terms "a" or "an", "one or more" and "at least one" can be used interchangeably herein unless otherwise expressly indicated otherwise.

As can be easily understood from the foregoing, the basic concepts of the present invention may be embodied in a variety of ways. The invention involves a skin laxity measuring system which includes numerous and varied embodiments of a skin laxity measurement tool (1) and methods of measuring skin laxity.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "mark" should be understood to encompass disclosure of the act of "marking"—whether explicitly discussed or not—and, conversely, were there effectively disclosure of the act of "marking", such a disclosure should be understood to encompass disclosure of "a mark" and even a "means for marking." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the skin laxity measurement tools herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A skin laxity measurement tool, comprising:
   a) a first linear measurement guide;
   b) a first arm fixedly coupled to said first linear measurement guide;
   c) a second arm coupled to said first linear measurement guide, said first arm and said second arm disposed to provide opposed inner surfaces in moveable relation, said first arm and said second arm correspondingly provide a first arm terminal and a second arm terminal disposed a distance from said first linear measurement guide; and
   d) a cross member slidely coupled to both said first arm and said second arm in substantially perpendicular relation to said opposed inner surfaces to allow positioning of said cross member at a location between said first arm end and said first arm terminal and said second arm end and said second arm terminal.

2. The skin laxity measurement tool described in claim 1, wherein said first arm slidely couples with said first linear measurement guide and said second arm fixedly couples to said first linear measurement guide to provide said opposed inner surfaces disposed in moveable relation.

3. The skin laxity measurement tool described in claim 1, wherein both of said first arm and said second arm slidely couple to said first linear measurement guide to provide said opposed inner surfaces disposed in moveable relation.

4. The skin laxity measurement tool described in claim 1, further comprising a first graduated scale coupled to said first linear measurement guide.

5. The skin laxity measurement tool described in claim 4, further comprising a second graduated scale coupled to said first arm or said second arm.

6. The skin laxity measurement tool described in claim 5, wherein said first graduated scale coupled to said first linear measurement guide comprises a plurality of measurement indicia in alignable relation to movement of said first arm to provide a distance value which corresponds to a distance between said opposed inners surfaces of said first arm and said second arm.

7. The skin laxity measurement tool described in claim 6, wherein said second graduated scale coupled to said first arm or said second arm comprises a plurality of measurement indicia in alignable relation to movement of said cross member to provide a height value corresponding to a height of said cross member from said first arm terminal and said second arm terminal.

8. The skin laxity measurement tool described in claim 5, wherein said first graduated scale coupled to said first liner measurement guide comprises a plurality of measurement indicia translatable by operation of a distance calculator to display said distance value.

9. The skin laxity measurement tool described in claim 8, wherein said second graduated scale coupled to said first or second arm comprises a plurality of measurement indicia translatable by operation of a height calculator to display said height value.

10. The skin laxity measurement tool described in claim 9, wherein said distance calculator comprises a digital distance calculator further comprising a calibration element which functions to calibrate said distance value against a pre-determined said distance between said opposed surfaces of said first arm and said second arm and said distance value.

11. The skin laxity measurement tool described in claim 10, wherein said height calculator comprises a digital height calculator having a calibration element which functions to calibrate said height value against a pre-determined said height between said cross member and said first and second arm terminals.

12. A method of skin laxity measurement, comprising the steps of:
   a) establishing a first location on an external surface of a skin of an animal;
   b) establishing a second location on said external surface of said skin of said animal, said skin between said first location and said second location capable of forming a tissue fold upon opposed forcible urging at each of said first location and said second location;
   c) providing a skin laxity measurement tool having a first arm coupled by a first arm end to a first linear measurement guide and a second arm coupled by a second arm end to said first linear measurement guide, said first arm and said second arm disposed to provide opposed inner surfaces in moveable relation, each of said first arm and said second arm correspondingly having a first arm terminal and a second arm terminal, and a cross member slidably engaged with said first arm and said second arm in substantially perpendicular relation to allow positioning of said cross member at a location between said first arm end and said first arm terminal and said second arm end and said second arm terminal;

d) contacting said external surface of said skin of said animal proximate said first location with said first arm terminal;

e) contacting said external surface of said skin of said animal proximate said second location with said second arm terminal;

f) applying sufficient opposed forcible urging of said first arm and said second arm to reduce distance between said opposed inner surfaces sufficient to generate a tissue fold between said opposed inner surfaces, said tissue fold having a tissue fold height and a tissue fold width;

g) determining a distance value for a distance between opposed inner surfaces of said first arm and said second arm in contact with said tissue fold and which corresponds to said tissue fold width;

h) positioning said cross member to contact said tissue fold; and i) determining a height value for a height between said terminal end of said first arm and said cross member in contact with said tissue fold and which corresponds to said tissue fold height.

* * * * *